United States Patent [19]

Trowbridge et al.

[11] Patent Number: 4,626,507

[45] Date of Patent: Dec. 2, 1986

[54] HYBRIDOMAS PRODUCING MONOCLONAL ANTIBODIES SPECIFIC FOR A HUMAN CELL SURFACE GLYCOPROTEIN

[75] Inventors: Ian S. Trowbridge, San Diego; M. Bishr Omary, Del Mar, both of Calif.

[73] Assignee: The Salk Institute for Biological Studies, San Diego, Calif.

[21] Appl. No.: 190,725

[22] Filed: Sep. 25, 1980

[51] Int. Cl.[4] .................. C12N 15/00; C12N 5/00
[52] U.S. Cl. .................... 435/240; 435/68; 435/172.2; 435/241; 935/103
[58] Field of Search .............. 435/240, 241, 172.2, 435/41, 68; 935/103

[56] References Cited

U.S. PATENT DOCUMENTS 4,172,124  10/1980  Koprowski et al. ............ 424/85
4,196,265   4/1980  Koprowski et al. ............ 435/2

OTHER PUBLICATIONS

Trowbridge, I. S., Interspecies Spleen-Myeloma Hybrid Producing Monoclonal Antibodies Against Mouse Lymphocyte Surface Glycoprotein, T22, *J. Exp Med.* 1978, pp. 313-323.

Melchers, et al., Second Workshop on Functional Properties of Tumors of T and B Lymphocytes, Apr. 3-5, 1978, Bethesda, Md. pp. IX-XIX.

Omary et al., Human Cell-Surface Glycoprotein with Unusual Properties, *Nature,* Aug. 1980, vol. 286, pp. 888-891.

C. Kohler and C. Milstein, Eur. J. Immunol., 1976, vol. 6, pp. 511-519.

*Primary Examiner*—Sidney Marantz
*Attorney, Agent, or Firm*—Fitch, Even, Tabin & Flannery

[57] ABSTRACT

Monoclonal antibodies are produced for a glycoprotein which is selectively expressed on the surface of human proliferating and immature hematopoietic cells but which is absent from normal peripheral blood cells. Mice are inoculated with human hematopoietic cells or fragments thereof, and spleen cells obtained from the mice are fused with mice myeloma cells to product hybridomas. The hybridomas are cultured as clones, and antibodies obtained from the individual clones are tested for their specificity for hematopoietic cells. Clones which produce antibodies specific for proliferating and immature hematopoietic cells are selected for further culturing to produce the antibody, and the antibody is obtained from the culture growth medium or from ascitic fluid of mice bearing the hybridoma tumor.

11 Claims, No Drawings

HYBRIDOMAS PRODUCING MONOCLONAL ANTIBODIES SPECIFIC FOR A HUMAN CELL SURFACE GLYCOPROTEIN

This invention was made with Government support under Grant No. CA-17733 awarded by the National Institutes of Health. The Government has certain rights in this invention.

The present invention is directed to monoclonal antibodies and more particularly to monoclonal antibodies which distinguish between human proliferating and immature hematopoietic cells and normal peripheral blood cells.

BACKGROUND OF THE INVENTION

Antibodies have long been used in medical diagnosis, e.g., determining blood types, and in biological experimentation. The usefulness of antibodies, however has been somewhat limited, as their complexity and diversity have made it very difficult to obtain homogeneous antibodies. Antibodies are complex protein or protein-based molecules which are produced by the immune systems of animals to protect the animal against foreign substances. Antibodies for medical use are generally obtained by injecting an animal with a foreign substance which will stimulate the animal's immune system and, most commonly, isolating an antibody fraction from the peripheral blood serum or from the ascitic fluid. The antibody fraction contains antibodies specific to the injected foreign substance as well as various other antibodies produced by the animal, and by known techniques, it may be possible to substantially isolate an antibody specific to the particular foreign substance. However, even when an antibody for a particular foreign substance is isolated, such antibody is actually a mixture of several antibodies which recognize various antigenic determinants of the foreign substance or related substances. While some individual antibody molecules may be highly specific, recognizing only a certain foreign substance or portion thereof, other antibody molecules may be less selective, recognizing not only the subject foreign substance but other substances as well. Because it is generally practically impossible to separate all related antibodies, even the most carefully purified antibody fractions may react with more than one substance.

In recent years, techniques of producing monoclonal antibodies have been developed which make it possible to obtain homogenous, highly specific antibodies. Generally, such antibodies are produced by immunizing an animal with a protein fraction or other foreign substance, obtaining antibody-producing cells from the animal, and fusing the antibody-producing cells with strains of myeloma cells, e.g., tumor cells, to produce hybridomas which are isolated and cultured as monoclones. The monoclonal hybridomas may either be cultured in vitro or may be grown as tumors in a host animal. Because each antibody-producing cell produces a single unique antibody, the monoclonal cultures of hybridomas each produce a homogeneous antibody which may be obtained either from the culture medium of hybridoma cultures grown in vitro or from the cells, ascitic fluid, or serum of a tumor-bearing host animal.

Not all of the hybridoma clones which result from fusing neoplastic cells with antibody-producing cells are specific for the desired foreign substance or antigen (a substance with which the antibody reacts) because many of the hybridomas will make antibodies which the animal has produced to react with other foreign substances. Even antibodies against the subject antigen will differ from clone to clone because antibodies produced by different cells may react with different antigenic determinants of the same molecule. From each clone, therefore, it is necessary to obtain the resulting antibody or the antibody-containing medium, serum or ascitic fluid and test its reactivity with the subject antigen and to test its specificity by determining with what other substances, if any, it recognizes. While the necessity of characterizing the antibody of each clone adds to the complexity of producing monoclonal antibodies, the wide variety of homogeneous antibodies which may be obtained gives investigators a number of very precise tools to map the structure and development of somatic cells.

The availability of homogeneous, highly specific monoclonal antibodies dramatically increases the value of antibodies as a diagnostic, experimental and therapeutic tool. Use of monoclonal antibodies for tumor and virus detection has been described in U.S. Pat. Nos. 4,172,124 and 4,196,265.

Monoclonal antibodies are particularly suitable for studying the pathways and processes by which cells differentiate into different types of somatic cells to produce the various tissues of the body. Cell differentiation is a complex subject, and understanding of the processes are only beginning. Proteins which are specific to particular cell types and which may be detected by different monoclonal antibodies, serve as precise markers for the study of cell development and differentiation. Monoclonal antibodies which are specific for given proteins not only may be used to ascertain the presence of known proteins in a cell, but may be used to detect substances heretofore undiscovered. Theoretically it may be possible to eventually obtain monoclonal antibodies for every macromolecule in the body to permit the complete mapping of the various proteins, etc.

An important topic in the field of cell differentiation is the study of cells which, in their mature form, are non-proliferating, being derived from actively proliferating stem cells. Many examples of such cells may be found in the peripheral blood. Red blood cells and leukocytes arise from stem cells in the bone marrow and both are normally non-proliferating as mature cells in the blood stream. Misdevelopment of somatic cells may lead to cancers, including blood cell-related cancers such as myelomas and leukemias, and monoclonal antibodies are useful for determining the proteins present in such cell to more fully trace their development and derivation.

It is a primary object of the present invention to create and culture hybridomas which produce monoclonal antibodies that differentiate between mature nucleated peripheral blood cells and proliferating and immature hematopoietic cells.

SUMMARY OF THE INVENTION

Monoclonal antibodies are produced which are specific for a cell surface glycoprotein, B3/25 with defined chemical properties that is found on hematopoietic cell lines but which is absent from mature peripheral blood cells. Mice are inoculated with a line of human hematopoietic cells, and spleen cells or lymph node cells are obtained from the inoculated mice and fused with mice tumors. Monocultures of the fused cells are produced, and the antibodies obtained from the monoclones are tested for their selectivity vis-a-vis hematopoietic cells and mature human nucleated peripheral blood cells to select the monocultures which produce antibodies with the desired characteristics. The monoclonal antibodies may be used to distinguish cells at various stages of development and may be used to detect and characterize cells which have developed abnormally, such as hematopoietic-derived tumor cells.

Other objects and advantages of the present invention will become apparent from the following detailed description of the invention.

DETAILED DESCRIPTION OF THE PREFERRED EMBODIMENTS

Monoclonal antibodies are produced which are specific for a glycoprotein, B3/25, which is found on the surface of hematopoietic cells but which is absent from mature mononuclear cells in the peripheral blood. The glycoprotein B3/25 has been characterized as having a monomer molecular weight of about 110,000, as determined by its migration on SDS-polyacrylamide gel, and existing in its native state as a disulphide bonded dimer. B3/25 glycoprotein is acidic, binds to concanavalin A and wheat germ agglutinin, and is expressed on Hela cells and other nonhematopoietic tumor cell lines, but it does not appear in detectable amounts in liver, brain or kidney tissue, nor a variety of other normal adult human tissues.

Hematopoietic cells are introduced into animals, to induce the production of antibodies to proteins and glycoproteins, including B3/25, found on the surface of the hematopoietic cells. The animal chosen for inoculation is not critical, but it is preferred that the strain of animal be well characterized. Because various strains of murines, i.e., rats, mice, etc., are well characterized, and because various murine-derived neoplastic cells are also available as well-characterized cultures, mice are chosen for production of the antibodies hereindescribed, although it is to be understood that the invention is not limited to murine-derived antibodies.

BALB/c mice are inoculated intraperitoneally with $2 \times 10^6$ human hematopoietic cells from the cell line K562 (Lossio et al., Blood 45, 321-334, 1975) suspended in standard tissue culture media. After 2 weeks, the mice are inoculated with a booster of at least $10^6$ cells. Four days after the second inoculation, the mice are sacrificed and their spleens are taken. A spleen cell suspension is prepared in the manner taught by Gerhard et al., Eur. J. Immunol. 5, 720-725 (1975). The red blood cells are removed by lysing in 0.83% NH$_4$Cl for 15 minutes at 4° C., and the resulting cell suspension is washed by one centrifugation ($800 \times$ g) in heat-inactivated horse serum and one centrifugation in protein-free Dulbecco's modified Eagles medium.

Because the antibody-producing cells obtained from the spleen do not independently reproduce, and thus cannot be cultured, they are fused with cells which may be independently cultured either in vivo or in vitro so that the genetic and metabolic processes of the fused hybridomas have characteristics of each of the parent cells, and it is intended that certain of the cells obtained will have the capabilities to independently reproduce and to produce the antibody of the antibody-producing parent cell. Some tumor cells, particularly myeloma cells, may be advantageously fused with antibody-producing cells to provide viable antibody-producing cultures of hybridomas. Although it is not necessary, it is preferred that the tumor cells and antibody-producing cells be derived from the same species to enhance the likelihood that the genetic and biochemical properties of the parent cells will be compatible and thus produce viable hybridomas. A number of myeloma cultures have been characterized, and herein, the mice-derived non-antibody producing myeloma cell line S194/5.XX0.BU.1 Trowbridge, J. Exp. Med., 148, 313-323 (1978), samples of which are on deposit at the American Type Culture Collection where the cell line if assigned accession number of CRL-8837, are used to produce the hybridomas. It is to be understood that other tumor lines, which include but are not limited to P3, Y3, SP2/0, MPC-11 and their derivatives, may also be used. It is advantageous to select a myeloma line which does not produce antibody so that the resulting hybridoma will only produce antibody chains of the parent spleen or lymph node cell.

The myeloma cells are maintained in Dulbecco's modified Eagle's medium supplemented with 10% horse serum. $10^7$ myeloma cells and $10^8$ cells obtained from the mice immunized with K562 cells are resuspended for fusion in a 40% solution (v/v) of polyethylene glycol 1500 according to the methods of Trowbridge supra. Cell hybrids are selected in hypoxanthine-aminopterin-thymidine (HAT) medium, all growth in HAT medium being indicative of successful hybridization of mouse spleen and mouse myeloma cells, and their production of antibodies against the hematopoietic cells used to inoculate the mice is tested by the antibody-binding assay described by Williams et al., Cell 12, 663 (1977). Hybrid cells are cloned by the method of limiting dilution in Falcon microtiter plates.

Clones of hybridomas may be grown in vitro according to known tissue culture techniques such as is described by Cotton et al., Eur. J. Immunol. 3, 136 (1973). Alternatively, hybridomas may be grown in vivo as tumors in a histocompatible animal or in athymic nude mice. The antibodies may be recovered from the in vitro culture medium or from the serum or ascitic fluid of the animal by means known in the art, e.g. Gerhard et al., Proc. Natl. Acad. Sci., 75, pp. 1510-1514 (1978). In some cases it may be advantageous to obtain the antibodies directly from the cells of the culture or tumor.

The specificity of the antibody from each clone for hematopoietic cells vis-a-vis mature mononuclear peripheral blood cells is examined by the methods of Williams supra., and clones which produce antibody specific for hematopoietic cells are selected. When a useful hybridoma clone is produced, it is generally advantageous to reclone the cell line to avoid overgrowth of cultures with variant cells no longer producing antibody. Because the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and/or to produce the particular antibody. Accordingly, it is important, soon after the initial hybridization, that a hybridoma clone of interest is recloned to ensure the availability of functioning strains of the antibody-producing hybridoma. Two Cell line cultures, which each produce a monoclonal antibody specific for B3/25 glycoprotein, have been developed and are on deposit at the American Type culture Collection (ATCC) of 12031 Parklawn Drive, Rockville Md. and have been assigned the accession numbers CRL-8034 and CRL 8035.

Trace antibody-binding assays conducted according to the methods of Morris et al., *Eur. J. Immunol.* 5, 274–281 (1974) demonstrate the general reactivity of the B3/25 glycoprotein-specific monoclonal antibodies with human hematopoietic cells and non-reactivity with human peripheral blood leukocytes. B3/25 glycoprotein is determined not to be present on a significant fraction of thymocytes or normal bone marrow cells.

While the B3/25 glycoprotein may be characterized by its expression on proliferating and immature human hematopoietic cells and its absence from human mononuclear peripheral blood cells, it is not tissue-specific because it is found on tumor cells derived from nonhematopoietic cells as well. Rather, its expression seems to be related to cell proliferation. In cases where the glycoprotein is expressed in normal proliferating cells, e.g., lymphoblasts, it is absent from the corresponding mature, non-reproducing cells, e.g., peripheral lymphocytes. Similarly, the presence of B3/25 glycoprotein in tumor cells appears to be generally cell-stage related. B3/25 glycoprotein is expressed in hematopoietic tumor cell lines but is absent from most peripheral blood leukemic cells. B3/25 glycoprotein is, however, expressed in small proportions in the peripheral blood of some patients with acute myeloid leukemia.

The following example is further evidence of the cell-stage dependent nature of the B3/25 glycoprotein.

EXAMPLE

Hybrids are produced by mixing $10^8$ spleen cells obtained from BALB/c mice immunized with K562 hematopoietic cells with $10^7$ S194/5.XX0BU.1 cells. The cell mixture is centrifuged at 800× g, and the cells are resuspended for fusion in a 40% (v/v) solution of polyethylene glycol 1500 in modified Eagle's medium. Cell hybrids are selected in HAT medium and cloned by the method of limiting dilution in microtiter plates.

A resulting monoclonal cell line, produced a B3/25 glycoprotein-specific monoclonal antibody which is used to study the B3/25 expression on HL-60 cells. HL-60 cells are of a promyelocytic tumor cell line which may be induced by a variety of agents, including dimethyl sulfoxide (DMSO) to differentiate along the myeloid pathway to a more mature cell stage.

HL-60 cells are routinely maintained in RPM1 1640 medium supplemented with 10% fetal calf serum and 50 µM 2-mercaptoethanol. The cells are harvested and resuspended at $2 \times 10^5$ cells per ml. in fresh culture medium alone or containing 1.25% (v/v) DMSO. After growth for 5 days, the cultures are harvested, and binding of B3/25 monoclonal antibody to noninduced and induced HL-60 cells is determined by a trace antibody-binding assay employing $^{125}$I-labeled affinity-purified rabbit F(ab')2 anti-mouse IgG antibody essentially as described by Morris et al., supra. In the negative control for nonspecific binding, tissue culture medium is substituted for culture supernatant containing B3/25 antibody. Binding of a monoclonal antibody designated A3/10, which reacts with a common antigenic determinant on HLA molecules, is used as a positive control. $5 \times 10^5$ cells are used per assay and the results below represent the average of duplicate determinations.

| HL-60 Sample | Counts per minute × $10^3$ |
|---|---|
| noninduced control | 1 |
| noninduced HLA | 16 |
| noninduced B3/25 | 14 |
| induced control | 1 |
| induced HLA | 14 |
| induced B3/25 | 1 |

The virtual disappearance of B3/25 glycoprotein in the induced differentiated, HL-60 line is demonstrative of the presence of B3/25 glycoprotein in actively proliferating and immature cells and the disappearance of the glycoprotein as the cell differentiates toward a more mature form.

Because of the correspondence between B3/25 glycoprotein and cell stage, B3/25 glycoprotein specific antibodies are an important investigative tool useful in studying the derivation and development of tumor and leukemia cells. The presence or absence of B3/25 glycoprotein in tumor cells appears to be indicative either of the normal cell line from which they are derived or of the cell stage of differentiating tumor lines. In many leukemias, for example, it is believed that the peripheral blood cells are non-proliferating, being derived from lines of rapidly proliferating stem cells, and the observed absence of B3/25 glycoprotein in most peripheral leukemic cells supports this theory. B3/25 monoclonal antibodies may be used in locating lines of leukemic stem cells and in defining their normal counterparts.

Because B3/25 glycoprotein is expressed in certain cancer tumors, B3/25 antibody is applicable for various cancer diagnostic applications. Because B3/25 glycoprotein is generally not expressed in the peripheral blood cells, the presence of B3/25 glycoprotein-containing cells in the bloodstream, as determined by radioimmunoassay, may indicate the presence of cancer cells. Due to the highly specific nature of monoclonal antibodies, individual cancer cells may be complexed with radioactively labeled antibody and detected, as by autoradiography, before the cancer is detectable by conventional methods. Immunofluorescence techniques using the B3/25 glycoprotein-specific antibody are useful in determining the source and type of cancer cell in tumor biopsy. $^{125}$I-labeled monoclonal B3/25 glycoprotein-specific antibody may be used to detect metastases by X-ray imaging as described by Levine, et al., *Science*, 206, 844–846 (1979).

Potential therapeutic applications of B3/25 monoclonal antibodies include conventional immunotherapy, where a class of antibody is used to destroy the tumor cells by complement-mediated lysis or other effector mechanisms, and immunotherapy where a cytotoxic agent, such as methotrexate or ricin toxin, is carried by the monoclonal antibody to destroy tumor cells. Before such antibodies may be used for immunotheraphy, or for internal diagnostic applications, potential adverse antibody reactions with minor populations of normal cells must be investigated and overcome.

Modifications obvious to one with ordinary skill in the art may be made without departing from the scope of the present invention. For example, antibody production may be induced in the host animal by inoculating the animal with other human cell lines containing the glycoprotein or with cell membrane-derived fragments or cell-membrane-derived material rather than with complete hematopoietic cells. While the invention has been described in terms of human B3/25 glycoprotein, the methods are equally applicable to producing antibodies useful in detecting related non-human glycoprotein.

Various features of the invention are set forth in the following claims.

What is claimed is:

1. A cell line, produced by the fusion of an antibody-producing animal cell obtained from a rodent inoculated with human cellular material and a neoplastic cell, which produces a monoclonal antibody which reacts specifically with an acidic glycoprotein characterized by its presence on human proliferating and immature hematopoietic cells and its absence from normal human peripheral blood cells, said glycoprotein having a monomer molecular weight of about 110,000, naturally occurring as a desulfide bonded dimer, binding to concanavalin A and wheat germ agglutinin, being expressed in Hela cells and other nonhematopoietic tumor cells, and not appearing in detectable amounts in normal adult human brain, liver or kidney tissue, said glycoprotein reacting with the antibody produced by the cell line deposited at the ATCC and assigned Accession No. CRL-8034 or the antibody produced by the cell line deposited at the ATCC and assigned Accession No. CRL-8035.

2. A cell line according to claim 1 wherein said antibody-producing cell is derived from the murine genus.

3. A cell line according to claim 1 wherein said neoplastic cell and said antibody-producing cell are derived from the same species.

4. A cell line according to claim 1 wherein said antibody-producing cells are selected from the group of murine spleen cells and murine lymph node cells.

5. A cell line according to claim 1 wherein said antibody-producing cells are BALB/c mouse spleen cells.

6. A cell line according to claim 1 wherein said neoplastic cells are myeloma cells.

7. A cell line according to claim 1 wherein said neoplastic cell is of the non-antibody-producing myeloma cell line, S194/5.XX0.BU.1 (ATCC Accession No. CRL-8837).

8. A cell line according to claim 1 wherein said neoplastic cell is non-antibody-producing.

9. A cell line according to claim 1 in combination with a standard growth medium.

10. The cell line according to claim 1 assigned ATCC Accession No. CRL-8034.

11. The cell line according to claim 1 assigned ATCC Accession No. CRL-8035.

* * * * *

UNITED STATES PATENT AND TRADEMARK OFFICE
CERTIFICATE OF CORRECTION

PATENT NO. : 4,626,507

DATED : December 2, 1986

INVENTOR(S) : Ian S. Trowbridge et al.

It is certified that error appears in the above-identified patent and that said Letters Patent is hereby corrected as shown below:

In the Abstract, line 7, change "product" to --produce--.

Column 4, line 9, change "if" to --is--.

Column 4, line 10, delete "of"

Claim 1, Column 7, line 16, change "desulfide" to --disulfide--.

Signed and Sealed this

Twenty-first Day of April, 1987

Attest:

DONALD J. QUIGG

Attesting Officer

Commissioner of Patents and Trademarks